US012564448B1

(12) United States Patent
Cao et al.

(10) Patent No.: US 12,564,448 B1
(45) Date of Patent: Mar. 3, 2026

(54) PEDICLE SCREW AND IMPLANT PLACEMENT PREDICTION ENGINE

(71) Applicant: Theseus AI, Inc., Los Angeles, CA (US)

(72) Inventors: Billy Cao, San Francisco, CA (US); Dave Harrison, San Francisco, CA (US); Luke Macyszyn, Los Angeles, CA (US); Sam Elhag, Los Angeles, CA (US); Marcus Karr, Redding, CA (US)

(73) Assignee: Theseus AI, Inc., Los Angeles, CA (US)

( * ) Notice: Subject to any disclaimer, the term of this patent is extended or adjusted under 35 U.S.C. 154(b) by 0 days.

(21) Appl. No.: 19/183,062

(22) Filed: Apr. 18, 2025

Related U.S. Application Data

(63) Continuation of application No. 18/652,811, filed on May 1, 2024, which is a continuation-in-part of application No. 18/419,547, filed on Jan. 22, 2024, which is a continuation-in-part of application No. 17/976,785, filed on Oct. 29, 2022, which is a
(Continued)

(51) Int. Cl.
| | |
|---|---|
| *G06K 9/00* | (2022.01) |
| *A61B 34/10* | (2016.01) |
| *G16H 10/60* | (2018.01) |
| *A61B 34/20* | (2016.01) |

(52) U.S. Cl.
CPC ............. *A61B 34/10* (2016.02); *G16H 10/60* (2018.01); *A61B 2034/2055* (2016.02)

(58) Field of Classification Search
CPC ...... A61B 34/10–2034/108; A61B 2034/2055; A61B 17/70–7098; A61B 5/7485; G16H 10/60; G06T 2207/30012; G06T 7/10–194; G06T 2207/20021; G06T 2207/20112–20168; G06T 2207/20081; G06T 2207/20084; G06T 9/002; G06T 5/60; G06V 10/25–273; G06V 20/49; G06V 20/695; G06V 40/162; G06V 20/80; G06V 20/698; G06V 10/70; G06V 10/82; G06V 10/774–7796; G06V 10/454; G06K 9/6224; G06K 9/6256; G06K 9/6257; G06K 9/6259; G06N 3/02–126; G06N 20/00–20; G06F 18/214–2155; G06F 7/023; G06F 40/16; G01N 29/4481

See application file for complete search history.

(56) References Cited

U.S. PATENT DOCUMENTS

| | | |
|---|---|---|
| 9,020,235 B2 | 4/2015 | Krishnan et al. |
| 9,317,926 B2 | 4/2016 | Wang et al. |

(Continued)

OTHER PUBLICATIONS

International Search Report for PCT Application No. PCT/US2020/033659, mailed Aug. 8, 2020.

(Continued)

*Primary Examiner* — Atiba O Fitzpatrick
(74) *Attorney, Agent, or Firm* — Clause Eight; Michael Catania

(57) ABSTRACT

A computer-implemented method for placing pedicle screws is disclosed herein. The method inputs a medical image having at least one bone image which is then divided into spatial segments. A set number of screws are spaced in each segment according to a neural network trained on medical images of screw placement in a similar procedure.

4 Claims, 11 Drawing Sheets

Related U.S. Application Data continuation-in-part of application No. 16/878,533, filed on May 19, 2020, now Pat. No. 11,488,717.

(60) Provisional application No. 63/470,876, filed on Jun. 3, 2023, provisional application No. 63/464,556, filed on May 6, 2023, provisional application No. 63/443,380, filed on Feb. 4, 2023, provisional application No. 62/960,149, filed on Jan. 13, 2020, provisional application No. 62/894,818, filed on Sep. 1, 2019, provisional application No. 62/851,602, filed on May 22, 2019.

(56) References Cited

U.S. PATENT DOCUMENTS

| | | | |
|---|---|---|---|
| 9,940,711 B2 | 4/2018 | Bregman-Amitai et al. | |
| 10,039,513 B2 | 8/2018 | Bregman-Amitai et al. | |
| 10,111,637 B2 | 10/2018 | Bregman-Amitai et al. | |
| 10,140,543 B2 | 11/2018 | Dong et al. | |
| 11,871,967 B1 | 1/2024 | Woods | |
| 12,343,085 B2 * | 7/2025 | Mcguan | A61B 90/361 |
| 2007/0223799 A1 | 9/2007 | Weiss | |
| 2015/0100067 A1 * | 4/2015 | Cavanagh | A61B 5/064 |
| | | | 901/46 |
| 2015/0248593 A1 | 9/2015 | Nakashima et al. | |
| 2016/0073948 A1 | 3/2016 | Videman | |
| 2018/0061048 A1 | 3/2018 | Weiss | |
| 2019/0029757 A1 * | 1/2019 | Roh | A61B 5/748 |
| 2019/0133690 A1 | 5/2019 | Buerger et al. | |
| 2019/0146458 A1 * | 5/2019 | Roh | G05B 19/4099 |
| | | | 700/98 |
| 2020/0051274 A1 * | 2/2020 | Siemionow | A61B 34/10 |
| 2021/0045816 A1 | 2/2021 | Geist | |
| 2021/0145519 A1 * | 5/2021 | Mosnier | A61B 34/25 |
| 2022/0039875 A1 | 2/2022 | Choi et al. | |
| 2022/0265352 A1 * | 8/2022 | Zucker | G06T 7/12 |
| 2022/0351410 A1 * | 11/2022 | Siemionow | A61B 34/10 |
| 2023/0389896 A1 | 12/2023 | Maclean et al. | |
| 2024/0104727 A1 * | 3/2024 | Weede | G16H 30/40 |
| 2024/0138921 A1 * | 5/2024 | Roh | G16H 50/00 |
| 2024/0216067 A1 * | 7/2024 | O'Connor | G16H 50/50 |

OTHER PUBLICATIONS

Written Opinion for PCT Application No. PCT/US2020/033659, mailed Aug. 17, 2020.

Azimi et al., Lumbar Spinal Canal Stenosis Classification Criteria: A New Tool, Asian Spine Journal, 2015;9 (3):399-406, Sep. 3, 2015.

* cited by examiner

Placement Prediction Engine

Figure 3:
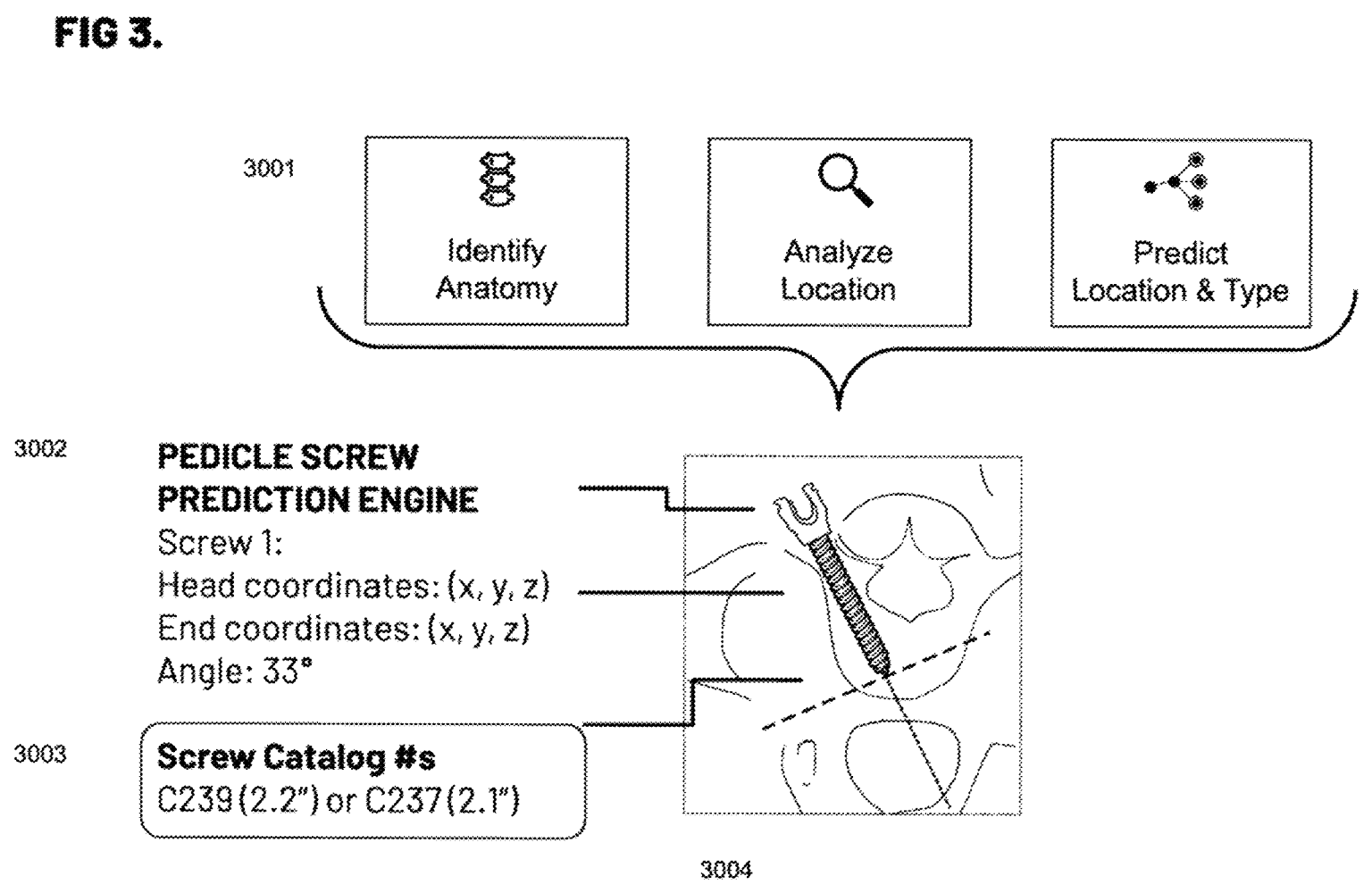

Identify Anatomy    Analyze Location    Predict Location & Type

3002

PEDICLE SCREW PREDICTION ENGINE

Screw 1:
Head coordinates: (x, y, z)
End coordinates: (x, y, z)
Angle: 33°

3003

Screw Catalog #s
C239(2.2") or C237(2.1")

3004

4001 Pedicle Screw

4002 Fusion Cage

4003 Screws & Rods

4004 Cages

4005 Plates

FIG 5.    Ruleset Example: Evidence–based screw dimension optimization

*The Optimal Screw Length of Lumbar Pedicle Screws during Minimally Invasive Surgery Fixation*

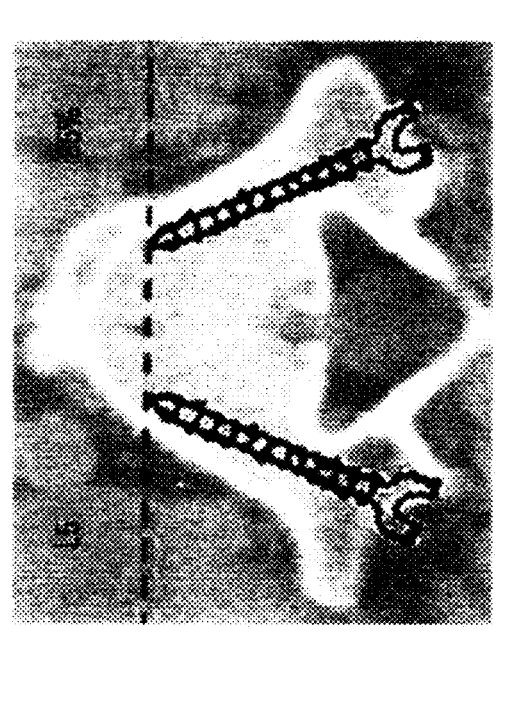

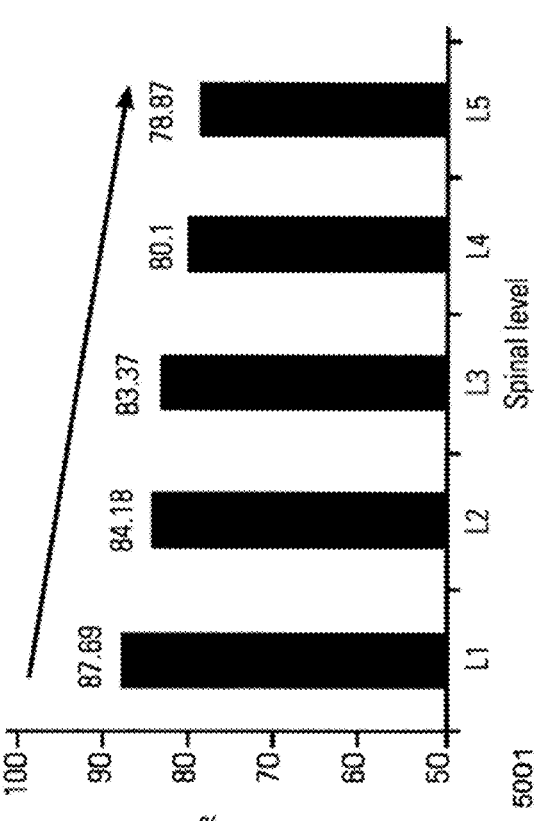

Chua MJ, Siddiqui S, Yu CS, Nolan CP, Oh JY. The Optimal Screw Length of Lumbar Pedicle Screws during Minimally Invasive Surgery Fixation: A Computed Tomography-Guided Evaluation of 771 Screws. *Asian Spine J*. 2019;13(6)1936-941. doi:10.31616/asj.2018.0276

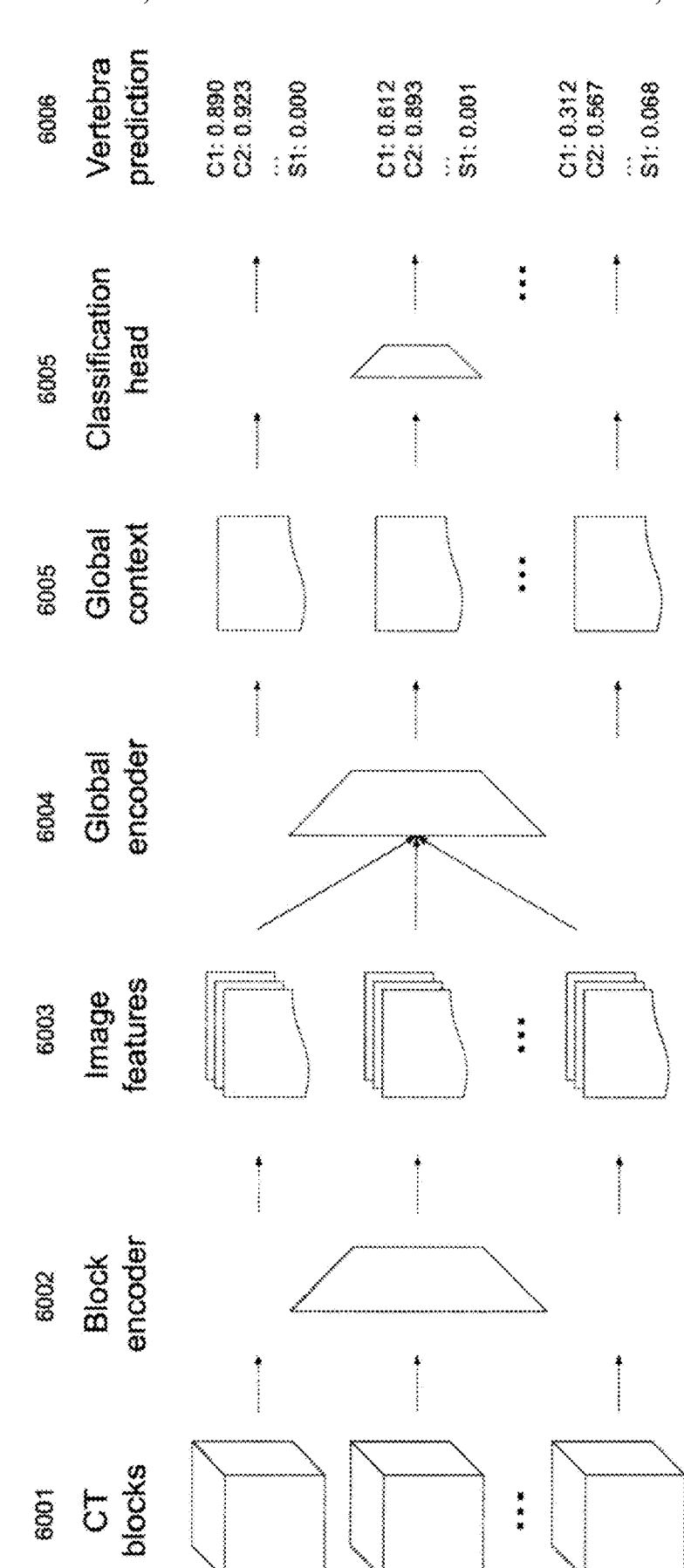
FIG 6. Prediction: Global Encoder Diagram
*25 classes: C1 thru S1*

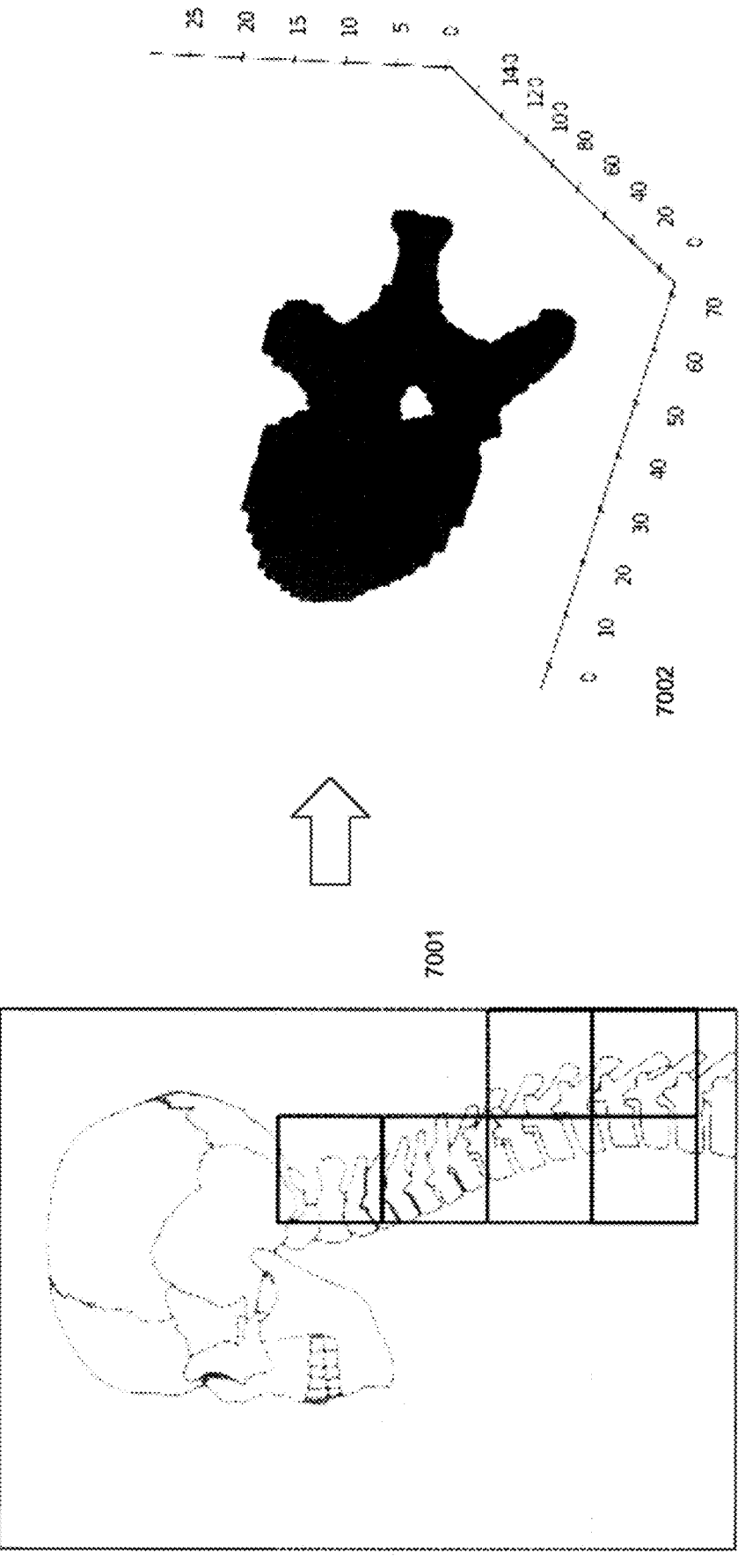
FIG 7.    Anatomical identification and segmentation

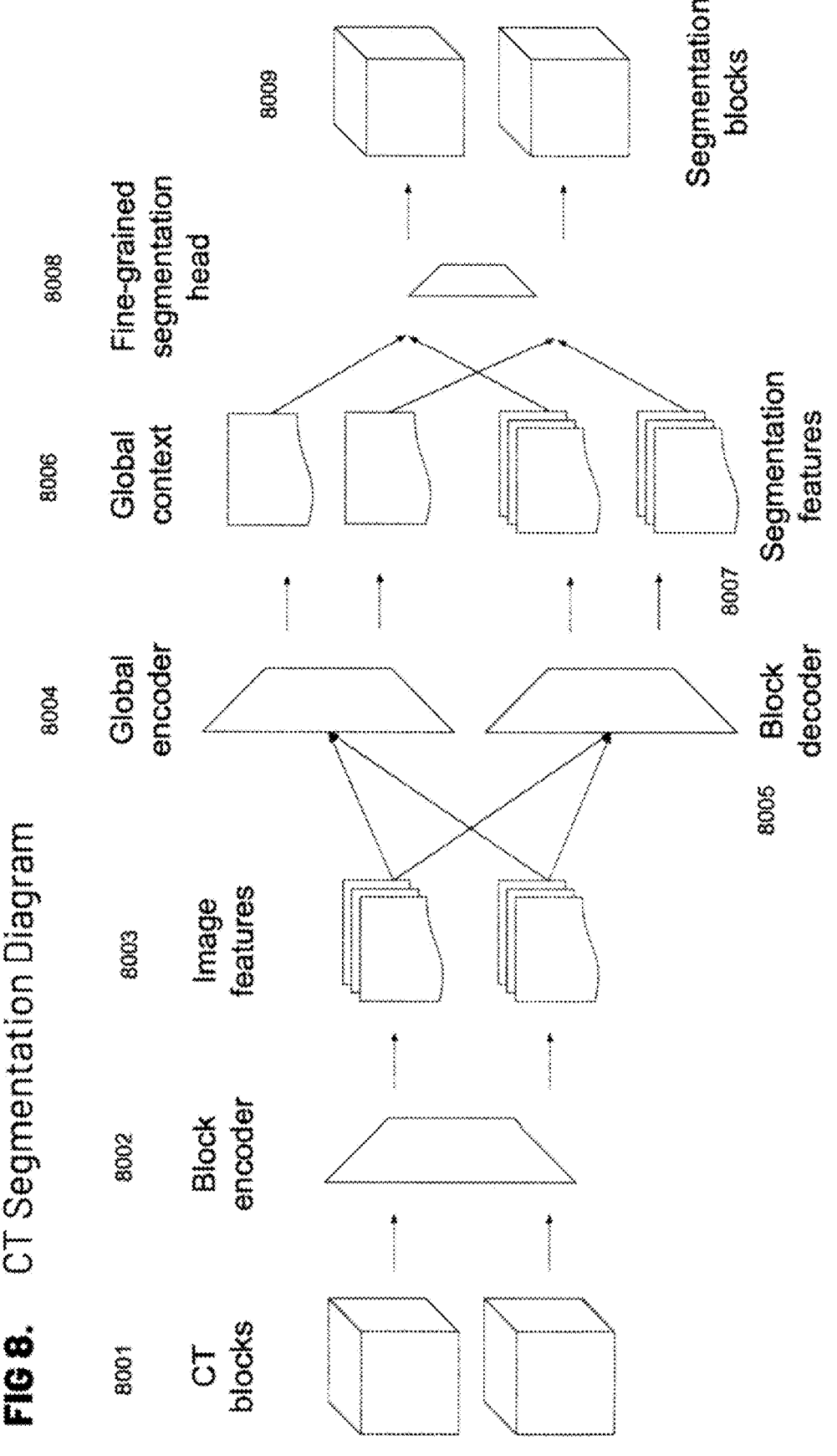
FIG 8.    CT Segmentation Diagram

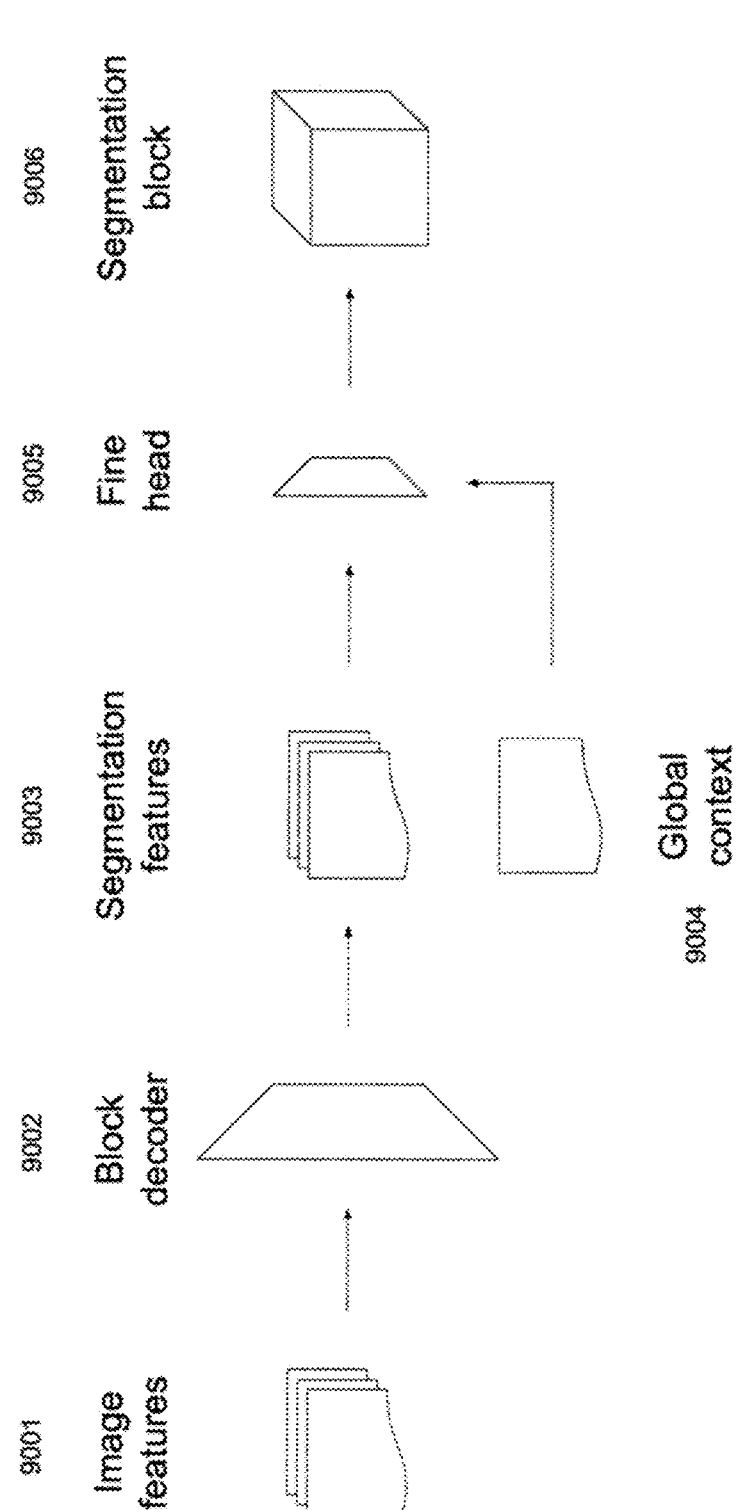
FIG 9.    Block Decoder Diagram for segmentation(26 classes: C1 thru S1)

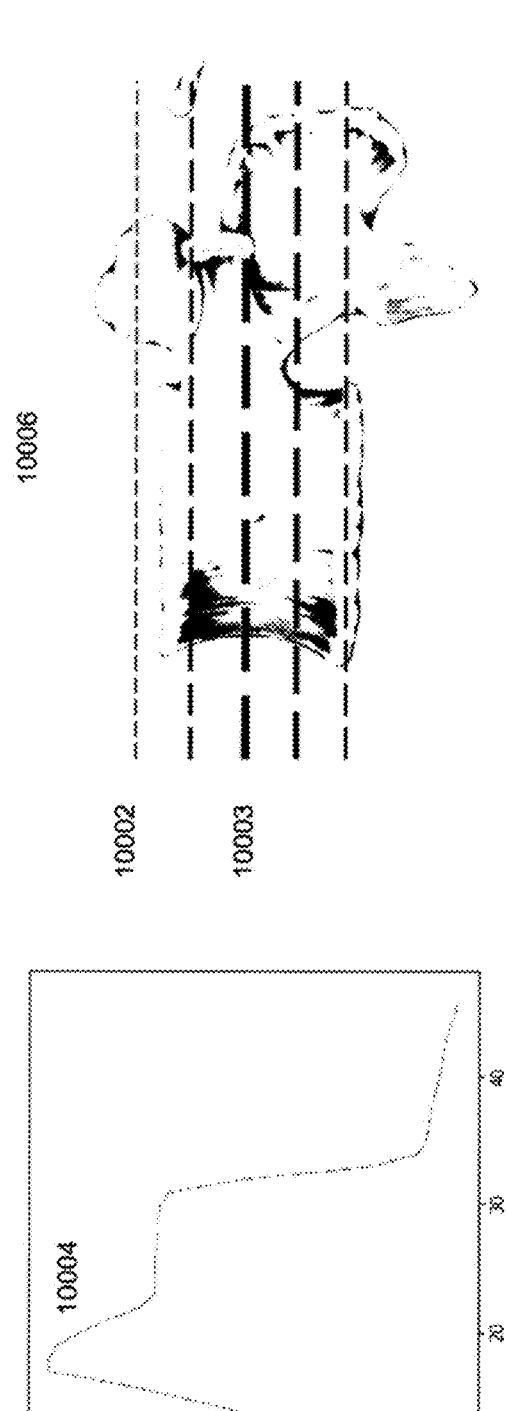
FIG 10. Finding the greatest area on the vertebral segmentation

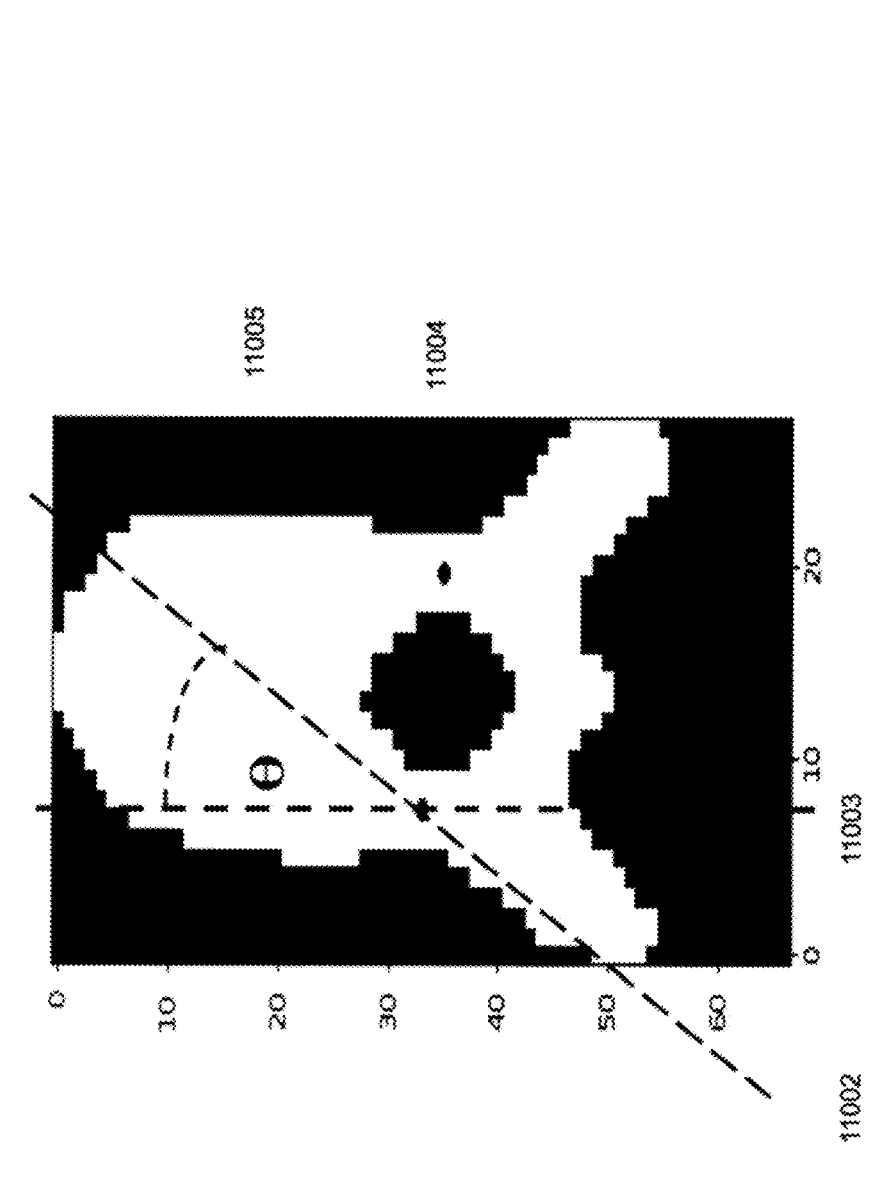
FIG 11. Select trajectory / angles with best score subject to desired constraints

PEDICLE SCREW AND IMPLANT PLACEMENT PREDICTION ENGINE

CROSS REFERENCES TO RELATED APPLICATIONS

The Present Application is a continuation application of U.S. patent application Ser. No. 18/652,811, filed on May 1, 2024, which claims priority to U.S. Provisional Patent Application No. 63/464,556, filed on May 6, 2023, and U.S. Provisional Patent Application No. 63/470,876, filed on Jun. 3, 2023, and U.S. patent application Ser. No. 18/652,811 is a continuation-in-part application of U.S. patent application Ser. No. 18/419,547 filed on Jan. 22, 2024, which claims priority to U.S. Provisional Patent Application No. 63/443,380, filed on Feb. 4, 2023, now U.S. patent application Ser. No. 18/419,547 is a continuation-in-part application of U.S. patent application Ser. No. 17/976,785, filed on Oct. 29, 2022, which is a continuation-in-part application of U.S. patent application Ser. No. 16/878,533, filed on May 19, 2020, now U.S. Pat. No. 11,488,717, issued on Nov. 1, 2022, which claims priority to U.S. Provisional Patent Application 62/851,602, filed on May 22, 2019, now, U.S. Provisional Patent Application 62/894,818, filed on Sep. 1, 2019, now U.S. Provisional Patent Application 62/960,149, filed on Jan. 13, 2020, now, each of which is hereby incorporated by reference in its entirety.

STATEMENT REGARDING FEDERALLY SPONSORED RESEARCH OR DEVELOPMENT

Not Applicable

BACKGROUND OF THE INVENTION

Field of the Invention

The present invention generally relates to medical diagnoses, medical imaging, radiology imaging, surgical planning, automated image analysis, image processing, computer vision, artificial intelligence, pedicle screw placement, and medical device selection.

Description of the Related Art

Pedicle screws are used in spine surgery primarily to provide stabilization and support to the spinal column. They are commonly used in spinal fusion surgeries, where two or more vertebrae are joined together to eliminate motion and alleviate pain or correct deformities. By attaching rods and other hardware to the pedicle screws, surgeons can create an internal brace that holds the vertebrae in the desired position while the bones fuse together.

The correct placement of pedicle screws is essential to achieve the desired spinal stabilization and fusion while minimizing the risk of complications, such as nerve damage or hardware failure.

Failure rates for spinal surgery are estimated at 10-40%. In addition to the economic cost of these procedures, which can range from $30 k to $150 k, patients may suffer emotional distress and ongoing pain.

Before a surgery, the surgeon reviews the patient's medical history, imaging studies (e.g., X-rays, MRI, CT scans), and other diagnostic information to determine the appropriate surgical approach and screw placement. During surgery, the surgeon identifies anatomical landmarks including the pedicle and surrounding anatomy using both visual and tactile cues. This helps in determining the appropriate entry point and trajectory for the pedicle screw.

Surgical planning can be a time-consuming task for surgeons especially for robotic assisted surgeries. Typically, the surgeon must scroll through an MRI or CT image to identify the appropriate spinal level for surgery (e.g. L3-4, L4-5). Then, the surgeon must manually place each screw in the appropriate location, indicate the desired length and width, and determine the angular rotation.

Best practices, research data, or patient-specific medical data may not be readily available to a surgeon. Incorporating all relevant information into surgical planning may be tedious, time-consuming, or simply infeasible due to data availability or time constraints.

Software systems can incorporate more relevant data efficiently as well as perform measurements and calculations faster than a surgeon may do manually.

For example, research has examined the optimal screw placement length of lumbar pedicle screws during minimally invasive surgery. Per the research, "this study recommends that pedicle screws should not exceed 85% of the vertebral body length on the lateral view for L1, 80% for L2-L4, and 75% for L5; this will minimize the risk of anterior cortical breach yet maximize pedicle screw purchase for fixation stability."

Additionally, since many surgeons do not do planning until the day of a surgery, suppliers of pedicle screws and other devices must ensure that a large array of options are available to the surgeon. This creates inefficiencies and other inventory management challenges for the device manufacturers.

Similar problems around planning and placement exist for rods and other implant hardware as well as for other anatomical areas such as the knees and hips. As such, a generalizable method for processing medical imaging, identifying anatomical areas, and computing appropriate placement locations.

Surgical systems and related planning software may be limited by hardware or software constraints. For example, a hardware system may not have a dedicated video card. As a result, machine learning algorithms or other software running on the hardware may need to be optimized to use minimal computing resources.

In order to integrate with device manufacturer hardware or software, outputs are typically made available via an Application Programming Interface (API), python script, binary executable, Docker or similar container, or other software language.

BRIEF SUMMARY OF THE INVENTION

A first aspect of the present invention is a method to import and extract medical image sequences.

A second aspect of the present invention is a multi-staged imaging pipeline that can process medical imaging.

A third aspect of the present invention is detecting the spine using a machine learning model.

A fourth aspect of the present invention is locating the regions of interest such as a vertebral levels.

A fifth aspect of the present invention is accepting user input on desired regions or desired implant predictions (e.g. pedicle screws).

A sixth aspect of the present invention is segmenting regions of interest using a segmentation model.

A seventh aspect of the present invention is calculating or predicting the initial placement of pedicle screws or other hardware.

An eighth aspect of the present invention is adjusting the initial predictions based on constraints or rulesets (e.g. screw cannot penetrate spinal canal).

A ninth aspect of the present invention is presenting the hardware predictions within a medical imaging viewer.

A tenth aspect of the present invention is storing user inputs and modifications to the initial predictions.

An eleventh aspect of the present invention is an ability to output placement predictions to other systems (e.g. via an API).

Yet another aspect of the present invention is a computer implemented method for analyzing an image to determine hardware placement in a patient. The method includes receiving a digital image depicting at least one bone. The method also includes receiving a user selection comprising one or more anatomical areas for hardware placement. The method also includes dividing the image into a plurality of spatial segments. The method also includes determining which spatial segments depict bone anatomy. The method also includes selecting a plurality of bone spatial segments from the plurality of spatial segments, each of the plurality of spatial segments depicting at least one part of bone anatomy. The method also includes identifying one or more anatomical areas in each spatial segment. The method also includes applying a ruleset to at least one spatial segment comprising at least one selected anatomical area to determine optimal hardware placement for each selected anatomical area. The method also includes outputting the determined optimal hardware placement.

Yet another aspect of the present invention is a computer-implemented method for placing pedicle screws. The method includes inputting a medical image; the medical image comprising at least one bone image. The method also includes dividing the bone image into spatial segments. The method also includes determining which spatial segments depict bone anatomy. The method also includes placing a given number of screws in each spatial segment according to an algorithm that optimizes for placement objectives.

Having briefly described the present invention, the above and further objects, features and advantages thereof will be recognized by those skilled in the pertinent art from the following detailed description of the invention when taken in conjunction with the accompanying drawings.

BRIEF DESCRIPTION OF THE SEVERAL VIEWS OF THE DRAWINGS

FIG. 3 is an example of possible outputs from a pedicle screw prediction engine.

FIG. 5 is a chart of data on optimal screw length for spine surgery.

FIG. 6 is a diagram of a global encoder for making anatomical predictions.

FIG. 7 is a diagram of anatomical identification and segmentation.

FIG. 8 is a diagram of the segmentation process.

FIG. 9 is a block decoder diagram for segmenting vertebrae.

FIG. 10 is a diagram showing the greatest area on a vertebral segmentation.

FIG. 11 is diagram showing an example selection process for screw placement.

DETAILED DESCRIPTION OF THE INVENTION

Figure 1:
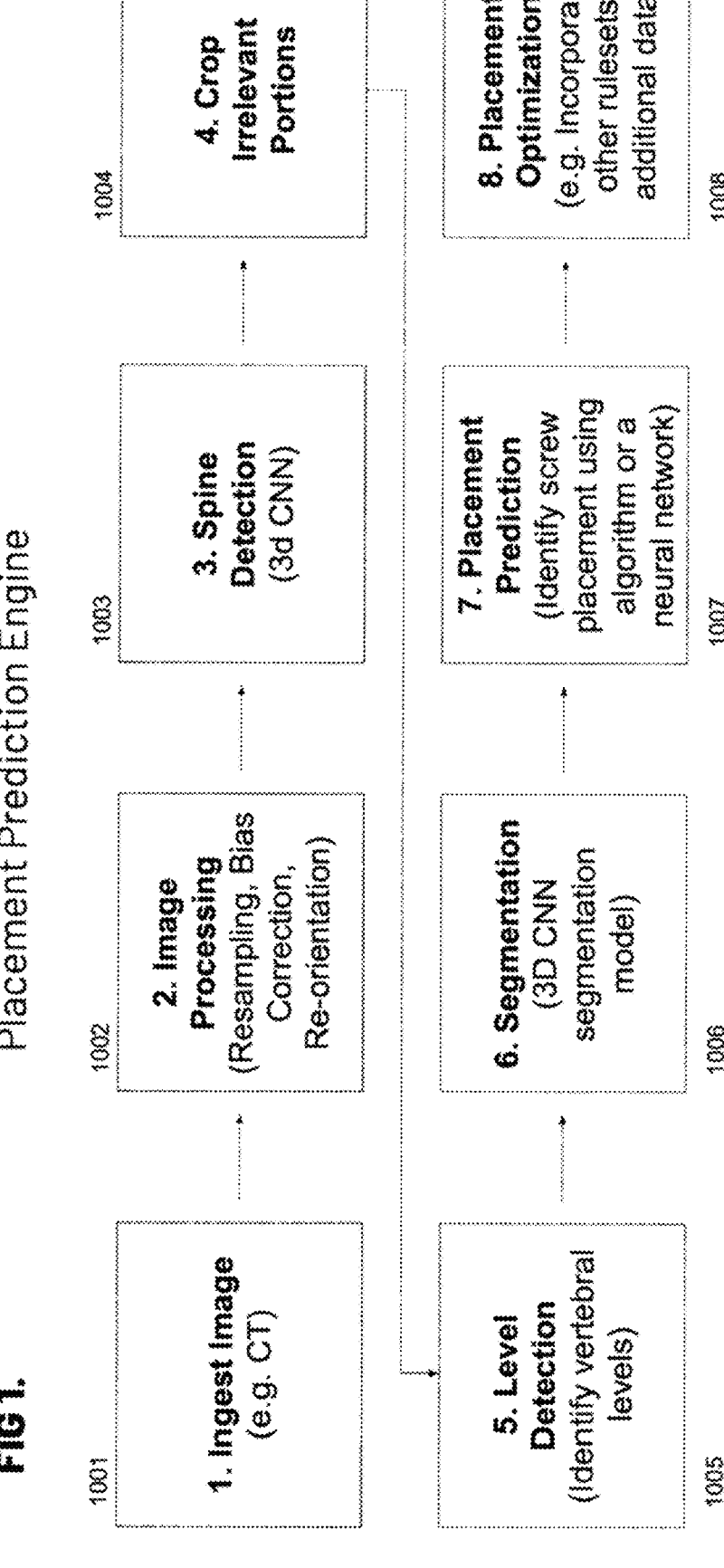
FIG. 1 is a flow diagram.

FIG. 1 is a flow diagram wherein an inputted medical imaging study in DICOM format such as a CT image is ingested 1001. The image is pre-processed by reorienting to a standard orientation, resampling to isotropic 1 mm voxel spacing volumes, histogram matching voxel values that enhance the contrast of bone anatomy, and then applying z-score normalization based on the summary statistics of a spine CT database 1002. Next, the spine is detected by applying a 3D convolutional neural network (CNN) to 48 mm $^3$ blocks to detect whether spinal anatomy is present in any given CT subvolume 1003. Based on these outputs, irrelevant portions of the scan are cropped 1004. To detect the spine levels, a transformer encoder is applied to the 48 mm $^3$ blocks of the cropped scan to determine which subvolumes contain which vertebral levels. Based on these outputs we locate the regions of interest relevant to user inquiries 1005. In each region of interest, we apply a 3D segmentation model with a hybrid CNN/transformer architecture to obtain high resolution, voxel-level masks of the vertebrae specified by the user 1006. The screw placement is calculated or predicted 1007 using angle, trajectory, or distance requirements or by applying a modified version of the segmentation model in 1006. Using the segmentations from 1006, the initial predictions are fine-tuned to meet constraints or rulesets such as: a) screw cannot penetrate spinal canal, b) screw angles must be symmetrical within some tolerance, c) screw placements at adjacent vertebral levels must be compatible with rod placements between them. These may be further constrained by user specified screw shapes and sizes, as might be found in a catalog 1008.

Figure 2:
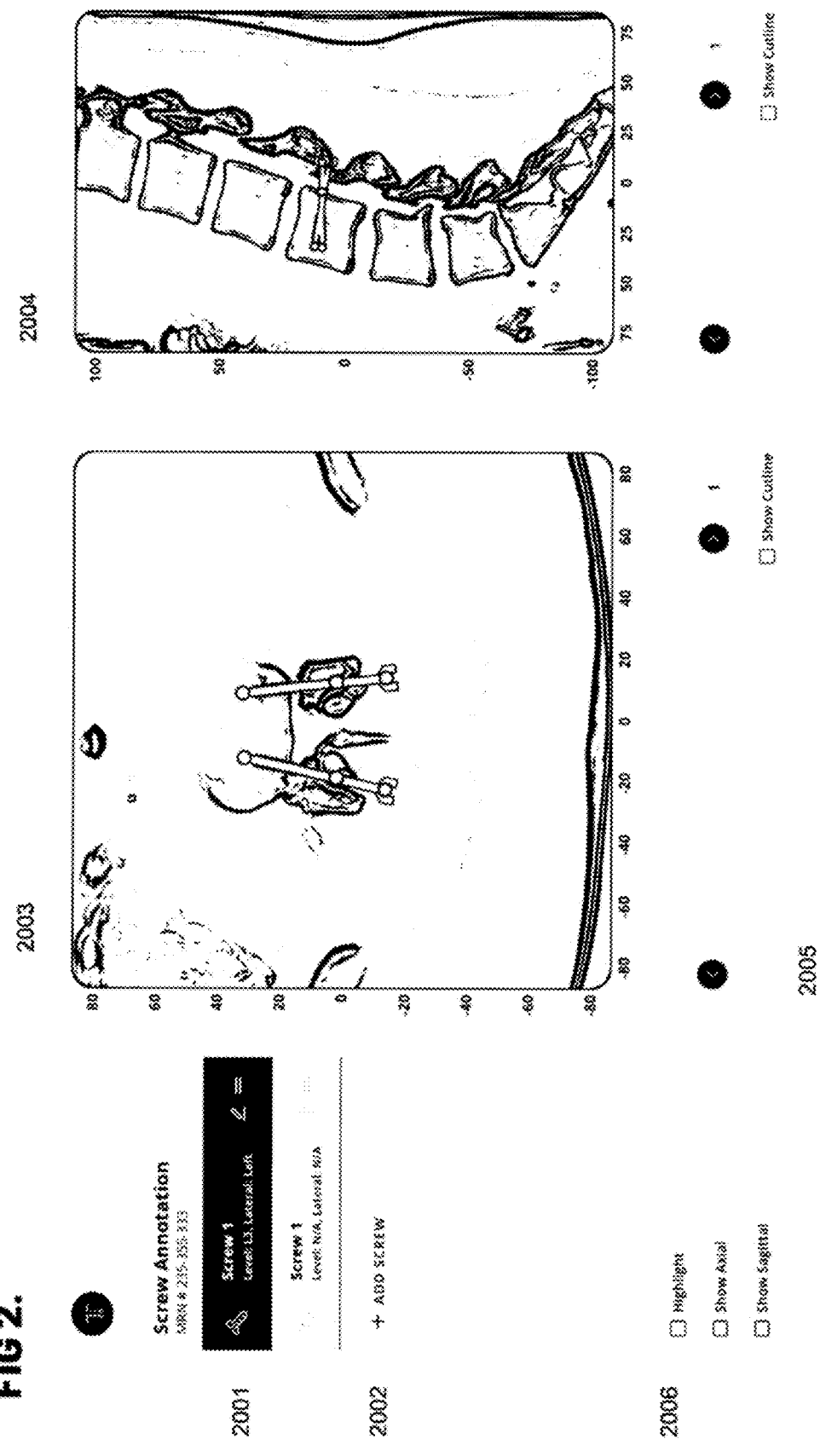
FIG. 2 is an example of surgical planning software with an integrated medical imaging viewer.

FIG. 2 is an example of surgical planning software with screw placement annotation 2001. The software may support inputs from a user such as adding another screw, modifying the screw location, 2002 or modifying the display of screws, visual overlays, or available imaging views 2006. The software supports viewing the user image in one or more views such as axial 2003 or sagittal 2004 to allow the user to see hardware placements as needed. A user can navigate through the images as desired 2005.

FIG. 3 summarizes the process of pedicle screw prediction as identifying the anatomy, analyzing the location, and predicting the hardware location and type 3001. The figure shows example outputs from the prediction engine which include screw coordinates and angle of insertion 3002 as well as recommended screws based on length, catalog, or other constraint 3003. The placement is visualized on an axial view of a spine 3004.

Figure 4:
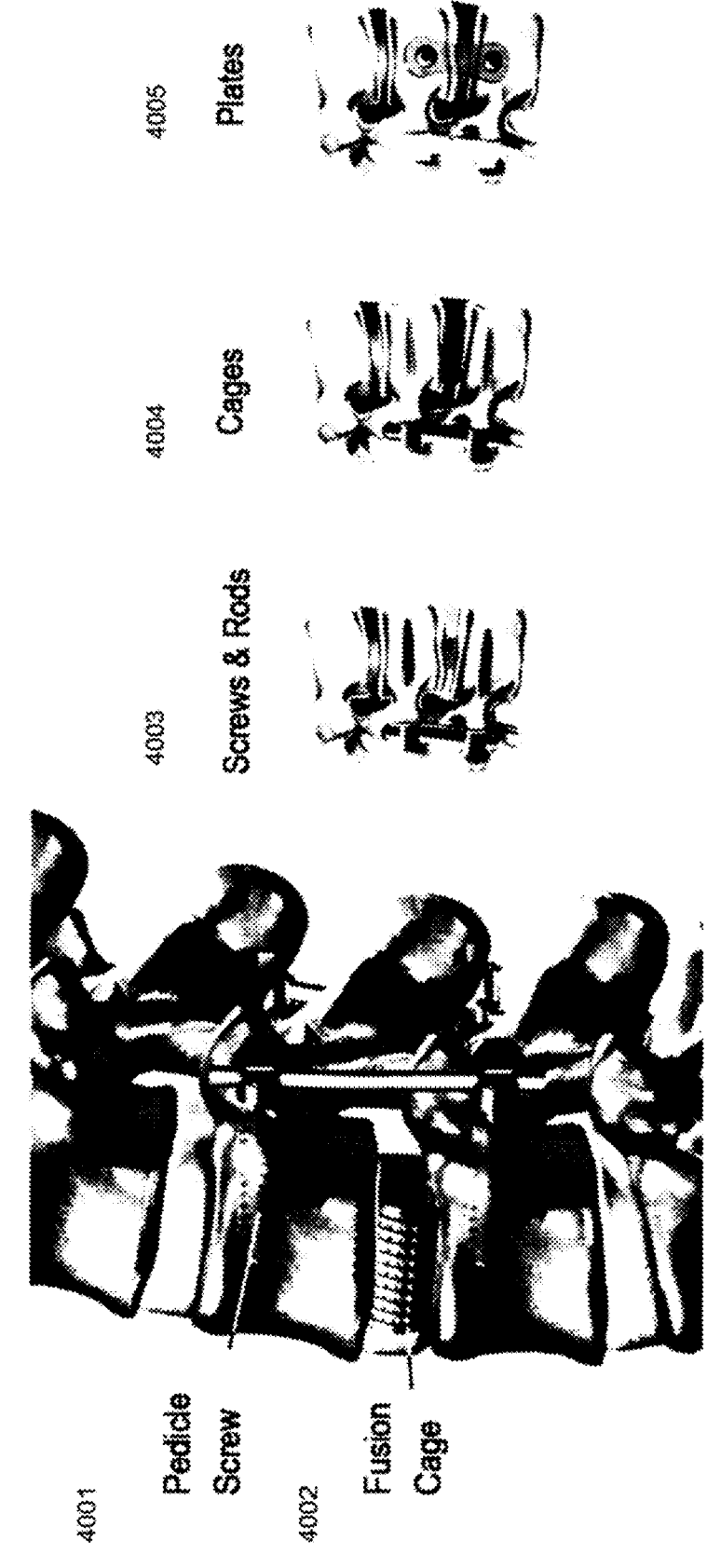
FIG. 4 is an illustration of example hardware used in spine surgery.

FIG. 4 is an illustration of various spine hardware that requires careful placement including pedicle screws 4001, a fusion cage 4002, screws and rods 4003, cages 4004, and plates 4005.

FIG. 5 is a chart of data from a research study that determined the optimal screw lengths for each spinal level 5001. An axial computed tomography image of L5 vertebral body is included showing a schematic drawing with optimal pedicle screw insertion in a medialized trajectory to 85% of the vertebral length 5002.

FIG. 6. shows a Global Encoder that is optimized for hardware constraints such as lack of a GPU or limited GPU. The pre-processed 3D imaging blocks (which are composed of resampled isotropic 1 mm voxel spacing volumes typically from CT scans) 6001 are fed into the block encoder 6002, which compresses the image into a limited set of features or embeddings 6003. These are then fed into the global encoder 6004 which reassembles the image features into a global context that is spatially and anatomically aware 6005. The classification 6005 then predicts which vertebra, if any, is in the CT block 6006.

FIG. 7. shows an example of a CT scan with blocks highlighted that have predicted values indicating presence of spine or specific vertebral levels (e.g. C1, C2, L4, L5) 7001. The relevant vertebrae in each selected block are then automatically segmented as shown in 7002, utilizing less compute power and time as compared to segmenting the whole scan.

FIG. 8. shows a segmentation process starting with the CT blocks 8001 which are fed into the block encoder 8002. The image features are extracted 8003 and sent to the global encoder 8004 and block encoder 8005. The global encoder sets a global context 8006 which is sent with the segmentation features 8007 to the fine-grained segmentation head 8008 which uses the global context 8006 to generate segmentation blocks that are aware of the vertebral level.

FIG. 9. shows a block decoder diagram for segmentation including classes for all vertebrae from C1 through S1. The image features 9001 are fed into the block decoder 9002 which generates the segmentation features 9003. The segmentation features and global context 9004 are fed into the fine head 9005 which generates the segmentation block with the vertebral predictions 9006. The original CT block 8001 and the segmentation block 9006 are identical, but for every voxel on the input, you now know whether the voxel belongs to a vertebrae.

FIG. 10. shows a plot of the areas along the vertical axis of the segmented vertebrae 10006 in order to determine the appropriate screw entry point. As an example, 10002 shows a limited overall area which is plotted around 10005 as compared to 10003 reaching the peak area at 10004.

FIG. 11. shows an example of screw trajectories through a vertebrae 11001. The screws may be placed at varying angles such as 11002 or 11003 to meet desired criteria such as passing through the centroid of the narrowest region of the bone 11004 while maximizing the length of the bone penetrated. The software may compute all lengths at each three dimensional angle of theta and output the optimal theta 11005. These are example placement criteria, but a different user may desire different criteria.

From the foregoing it is believed that those skilled in the pertinent art will recognize the meritorious advancement of this invention and will readily understand that while the present invention has been described in association with a preferred embodiment thereof, and other embodiments illustrated in the accompanying drawings, numerous changes modification and substitutions of equivalents may be made therein without departing from the spirit and scope of this invention which is intended to be unlimited by the foregoing except as may appear in the following appended claim. Therefore, the embodiments of the invention in which an exclusive property or privilege is claimed are defined in the following appended claims.

We claim as our invention the following:

1. A computer implemented method for analyzing an image to determine hardware placement in a patient, computer-implemented method performed by a computing device comprising a processor and a memory, the computer-implemented method comprising:

(a) receiving a digital image depicting at least one bone;

(b) pre-processing the received digital medical image by a transformation step including at least standardizing the volumetric resolution of the image via resampling:

(c) automatically identifying a region of interest within the pre-processed digital image by: (i) applying a first machine learning model trained for object detection to a plurality of spatial segments of the image to determine the presence and location of target anatomy; and (ii) cropping irrelevant portions of the image outside the detected target anatomy to create a reduced image for efficient processing:

(d) automatically identifying one or more target anatomical features within the reduced image by applying a second machine learning model trained for anatomical classification only to the reduced image;

(e) generating a high-resolution mask of each target bone component by applying a third machine learning segmentation model only to the identified one or more target anatomical features;

(f) determining optimal hardware placement for each target anatomical feature by: (i) applying a ruleset retrieved from a stored configuration to the generated mask, wherein the ruleset constrains placement by a catalog of available hardware and specified requirements; and (ii) predicting a screw trajectory that ensures the hardware does not penetrate a critical anatomical boundary;

outputting from the computing device the determined optimal hardware placement, including entry point coordinates and angle of insertion.

2. The method of claim 1 wherein the anatomical areas are vertebral levels.

3. The method of claim 1 wherein the hardware is pedicle screws.

4. The method of claim 1 wherein the first or second machine learning model incorporates a global encoder for reassembling image features into a global context for classification, and wherein the third machine learning segmentation model uses this global context to generate the segmentation mask.

* * * * *